United States Patent [19]
Greff

[11] Patent Number: 6,123,953
[45] Date of Patent: Sep. 26, 2000

[54] COSMETIC, DERMOPHARMACEUTICAL OR VETERINARY COMPOSITIONS FOR DISINFECTING HUMAN OR ANIMAL SKIN

[75] Inventor: Daniel Greff, Mere, France

[73] Assignee: STOA S.A., Perray-en-Yvelines, France

[21] Appl. No.: 09/125,350

[22] PCT Filed: Feb. 20, 1997

[86] PCT No.: PCT/FR97/00320

§ 371 Date: Aug. 18, 1998

§ 102(e) Date: Aug. 18, 1998

[87] PCT Pub. No.: WO97/30692

PCT Pub. Date: Aug. 28, 1997

[30] Foreign Application Priority Data

Feb. 21, 1996 [FR] France ................................. 96 02313
Feb. 23, 1996 [FR] France ................................. 96 05210

[51] Int. Cl.⁷ .................................................. A01N 25/24
[52] U.S. Cl. ........................... 424/407; 424/401; 424/405; 424/406; 424/438; 424/486; 424/487; 424/76.8; 424/78.18; 424/78.2; 424/78.31; 424/59; 424/62; 424/63; 424/65; 424/69; 424/78.05; 424/78.06; 424/78.07; 514/738; 514/944

[58] Field of Search .................................. 424/59, 62, 63, 424/65, 69, 76.8, 78.18, 78.31, 78.2, 78.05–78.07, 613, 667, 438, 401, 405–407, 409, 486, 487; 514/738, 944

[56] References Cited

FOREIGN PATENT DOCUMENTS

| | | |
|---|---|---|
| 0524548 | 1/1993 | European Pat. Off. . |
| 0584692 | 9/1994 | European Pat. Off. . |
| 0623336 | 11/1994 | European Pat. Off. . |
| 2125530 | 9/1972 | France . |
| 2678830 | 2/1993 | France . |
| 4320744 | 1/1995 | Germany . |
| 94/21234 | 9/1994 | WIPO . |

*Primary Examiner*—Neil S. Levy
*Attorney, Agent, or Firm*—Young & Thompson

[57] ABSTRACT

The use of alkane-1,2-diols for inactivating skin microorganisms by topical application includes 1,2-Octanediol used against the germs that cause acne and dandruff, as well as those that cause mastitis in dairy animals, and its activity strengthened by a synergistic interaction with gels such as glycerol poly(meth)acrylate.

16 Claims, No Drawings

COSMETIC, DERMOPHARMACEUTICAL OR VETERINARY COMPOSITIONS FOR DISINFECTING HUMAN OR ANIMAL SKIN

BACKGROUND OF THE INVENTION

Human or animal skin (that of mammals) is not sterile. It breeds either saprophyte germs which constitute the non-pathogenic and protective resident microflora, or parasitic pathogenic germs which are opportunistic, which can give rise to illness or more or less serious pathological conditions, especially if they succeed in penetrating tissue internally to colonize the blood or lymphatic system or internal organs.

Aspecticizing treatment of human and/or animal skin seeks its origins in the work of Pasteur and Semmelweiss; nowadays, there exist a large number of microbicidal molecules used for different applications: treatment of acne, treatment of capillary layers, different disinfection of small wounds (scrapes), disinfection of the hands of surgeons and the sick, disinfection of the udders of milk-giving animals to prevent mastitis.

The antimicrobial properties of 1,2-diol alkanes and 1,3-diol alkanes are known from EP-A-0524548, which also mentions their combination with aromatic alcohol for the preservation of cleaning agents for the skin, but with a decrease of germs only after several days.

The bacteriostatic effect of the compounds of the formula $R$-$CHOH$-$CH_2OH$ on gram positive bacteria and mold, is known from JP-A-51 091 327 for application to food products and seeds, or other industrial products.

SUMMARY OF THE INVENTION

The object of the present patent application is the discovery that the class of molecules of the general formula:

$$R-CHOH-CH_2-OH \quad (1)$$

in which R is a straighter branch chain alkyl of 3 to 12 carbon atoms, preferably straight chain of 6 to 8 carbon atoms, has a sufficiently strong microbicidal activity to be usable in treatments of the skin mentioned above. These alkane-diol molecules have been described as hydrating ingredients, as antimicrobial preservatives for the protection of cosmetic products; their topical use on the skin to fight pathogenic microbes has not been envisaged.

Moreover, it has been discovered that the combination of the alkane-diols with gels of the glyceryl polymethacrylate type, in a formula, is even more effective than each of the components alone.

French patent FR 2682296 has proposed a method of non-chemical preservation of cosmetic products or dermopharmaceuticals which is based on the use of gels of the glyceryl polymethacrylate type, whose property is to exert a strong osmotic influence on their environment, which permits inactivating the microorganisms introduced into a cosmetic preparation by depriving them of water. French patent 2.737.406 has proposed an improvement in the effectiveness of the method by associating polyols and a fluidizing agent for the polymethacrylate gel.

The object of the present patent application is that alkane-diols can be used in combination with the mentioned gels, at low concentrations, for the treatment of the problems of acne, skin troubles, impetigo, body odors caused by microorganisms, athlete's foot and other mycoses, microbial cutaneous afflictions in general, and the prevention of mastitis by topical application.

A gel of glyceryl polymethacrylate like those described in French patent 2682296 or 2678830, which inactivates the microorganisms introduced into a cosmetic preparation by depriving them of water, loses its activity when it is too dilute. However, when there is added an alkane-diol of formula (I), even at low concentration, there is noted an effect of inactivation of the germs, which is rapid and much stronger than the addition of the two substances would cause one to suppose. There is thus a synergy between the gel, with its osmotic power, and the alkane-diol, and its antimicrobial effect.

This is even more important because it permits decreasing the concentrations of diol necessary to obtain a microbicidal activity in the final products. The short chain alkane-diols can have slightly irritating properties, the usable concentration without risk is thus limited. The synergy with the gel permits overcoming this obstacle.

The gel of the glyceryl polyacrylate or polymethacrylate type is particularly important to product this synergy. It is comprised of glycerine (between 20 and 90%, preferably between 50 and 75% by weight), water (between 10 and 80%, preferably between 20 and 49% by weight) and polyacrylate and/or polymethacrylate (between 0.1 and 5% by weight) and has a viscosity comprised between 50,000 and 2,000,000 centipoise. This clathrate gel is characterized by its high power of water retention. It does not dry, even when exposed for months to ambient air or subjected to vacuum for 48 hours. This property is essential, the conventional hydrogels, the alginate gels, the polysaccharide gels, the cellulose gels or their derivatives or silicate gels do not satisfy this criterion. This gel is particularly effective to inactive the microorganisms with which it enters into contact, depriving the germs by its osmotic effect of water, which they need to survive.

The concentration of glyceryl polymethacrylate gel can vary between 1 and 99% by weight, preferably between 5 and 20% by weight.

This polymethacrylate is preferably selected from sodium, potassium, triethylamine, triethanolamine, ammonium, acrylic acid and/or methacrylic acid salts, but also from esters or amides of these acid polymers, or the cross-linked derivatives of the carbomere type (cross-linking with allyl ethers of pentaerythritol, of sugar or propylene, for exam- ple).

In cosmetic, dermopharmaceutical or veterinary compositions according to the invention, the concentration of the alkane-diol varies between 0.1 and 5% by weight, preferably between 0.1 and 1.0% by weight in the finished product.

Preferably, the alkane-diol is octane-1,2-diol.

The compositions of the present patent application can be used in any galenic form used in cosmetics, dermopharmaceuticals or veterinary application by topical application as an antiseptic or antimicrobial: aqueous solutions, water/oil and oil/water emulsions, milks, lotions, gels, pomades, capillary lotions, shampoos and rinses, soaps, sticks, sprays, poultices, dressings, this list being non- limiting.

The compositions according to the invention can moreover contain at least one fluidifying solvent of the general formula:

$$R_1-O-(R_2-O-R_2)_n-OR_3 \quad (II)$$

in which $R_1$ is a hydrogen atom or linear or branched chain C1-5 alkyl, R2 is linear or branched chain C1-5 alkyl, $R_3$ is a hydrogen atom or a linear or branched chain C1-5 alkyl and n is a whole number between 1 and 200,000.

Preferably, $R_1$ is linear C1-3 alkyl and n is a value between 1 and 3.

The proportion of fluidifying solvent is preferably comprised between 0.5 and 50% by weight, and more preferably between 1 and 10% by weight.

The compositions according to the invention also containing the mentioned fluidifying solvent, can be used unmixed or incorporated in other basic gels (carbomeres, as for example Carbopol® of Goodrich, or polysaccharide gels, alginates, xanthan gums, etc . . . ) at concentrations varying from 3 to 50% by weight, preferably between 10 and 20% by weight, for the treatment by immersion or massage of the teats of cows or other milk-giving animals.

The compositions containing these gels have the following advantages: they are colorless, thixotropic, which is to say the gel fluidifies in contact with the skin whilst leaving a hydrated film on the teat upon immersion; they do not contain preservatives or chemical disinfectants, they are non-toxic, non-irritating, they are strongly hydrating and soothing for the skin, and above all they have a high antimicrobial activity against germs found in the environment of the farm: *Staphylococcus aureus, Streptococcus faecalis, Pseudomonas aeruginosa, Escherichia coli, Lysteria monocytogenes* and numerous other maladies. This activity is due to the osmotic power of the gel, hence to a physical activity and to its combination with polyol or polyols.

DESCRIPTION OF THE PREFERRED EMBODIMENT

The invention will be illustrated by the following non-limiting examples:

EXAMPLE 1

Synergetic Effect alkane-diol alone:

1 ml of a suspension of Staphylococcus aureus ($75.0 \times 10^6$ germs/ml) is inoculated into 10 g of a solution of octane-1, 2-diol at a concentration of 0.2% in water.

After 30 seconds, 15 minutes and 30 minutes of contact, the number of revivifiable microorganisms is counted (spread on agar).

There is obtained: at 30 seconds: about $8.0 \times 10^6$ germs/ml, at 15 minutes: about $1.2 \times 10^6$ germs/ml, at 30 minutes: about 250,000 germs/ml, hence a bactericidal effect is noted at 30 minutes.

glyceryl polymethacrylate gel alone (at 40%)

With a procedure identical to the preceding, there is found the sum of germs inoculated after 30 seconds, 15 minutes and 30 minutes.

Inoculation with S. aureus: $3.0 \times 10^6$ germs/g: after 30 seconds, 3.1 x 106 germs/g, after 15 minutes $3.6 \times 10^6$ germs/g, and after 30 minutes $3.9 \times 10^6$ germs/g.

At 40% in water, this gel does not inactivate the tested microorganisms.

gel+alkane-diol:

A mixture of gel at 40% by weight in water and octane-1,2-diol containing 0.2% by weight leads to the following results:

Inoculation with S. aureus: $5.0 \times 10^6$ germs/g: after 30 seconds, there were $2.0 \times 10^4$ germs/g, after 15 minutes no revivifiable germ and after 30 minutes no revivifiable germ.

The effect of inactivation of the germs is hence a synergetic effect between the gel and its osmotic power and alkane-diol, because it is much stronger than the addition of the two substances would lead one to suppose.

EXAMPLE 2

Inactivation of germs responsible for acne, Propionibacterium acnes: 10 g of a carbomere gel containing 0.5% by weight of hexane-1,2-diol are inoculated with $4.8 \times 10^6$ germs/g of an anaerobic culture at 35° C. At time t=0, t=15 minutes and t=30 minutes, there are taken the counts of revivifiable germs.

There was no living germ, even at t=0 (maximum 30 seconds), whilst in the gel without hexane-1,2-diol, the germs proliferate (there were found between 3.0 and $8.0 \times 10^6$ germs/g).

An identical result is obtained for octane-1,2-diol against the yeast Pityrosporum ovale=Malassezia furfural rapid inactivation (at 15 minutes, the logarithmic reduction is by a factor of 5).

Topical use of a product containing an alkane-1,2-diol according to the invention has been tested under the following conditions:

10 volunteers having symptoms of juvenile acne used an aqueous solution containing 1% by weight of octane-1,2-diol for a period of 3 weeks. Clinical study before and after the treatment showed a substantial improvement of the condition of the skin at the treated sites, in comparison with untreated sites. Decrease of bacterial flora, fewer pustules, papules, blackheads; skin less greasy and smoother.

Another study was carried out on a farm: 20 cows of a herd of 40 lactating cows were treated twice a day by immersion of the teats in an aqueous solution containing 1% by weight of decane-1,2-diol, 3% by weight of glycerine, 2% by weight of polysorbate 20 (Tween® 20) and water as an excipient qsp 100%. After two months of treatment, the quantity of subclinical mastitis and of leucocytes in the milk decreased significantly in the treated cows in comparison with the other untreated half of the herd.

The antimicrobial protective effect of alkane-1,2-diols by topical application has thus been demonstrated for new uses.

The compositions according to the present invention can be combined with any other ingredient conventionally used in the field of cosmetics, dermopharmaceuticals or veterinary preparations; extraction lipids and synthesized lipids, gel-forming polymers and thickeners, surface active agents and emulsifiers, hydra or liposoluble active principles, plant extracts, tissue extracts, marine extracts, polyols, softeners, and other antimicrobial agents.

For compositions for the protection of udders against mastitis, there can be cited the following formulations:

EXAMPLE 3

| | |
|---|---|
| Carbopol (R) 934 (Goodrich) | 0.2 |
| Glyceryl polyacrylate | 5 |
| Glyceryl polymethacrylate | 5 |
| Butylene glycol | 5 |
| Ethoxyethanolacetate | 4 |
| Ethylhexyglycol | 1 |
| Water | qsp 100 |
| Triethanolamine | qsp pH5. |

EXAMPLE 4

| | |
|---|---|
| Carboxymethyl cellulose | 0.5 |
| Glyceryl polymethacrylate | 20 |
| Polyethylene glycol PEG 400 | 5 |
| 1,2 Pentanediol | 1.5 |
| Sorbitol | 10 |

| | -continued | |
|---|---|---|
| Water | | qsp100 |

EXAMPLE 5

| Carbopol (R) 940 (Goodrich) | 0.2 | |
|---|---|---|
| Glyceryl polyacrylate | 15 | |
| Ethoxydiglycol | 4 | |
| Octane-1,2-diol | 1 | |
| Water | gsp | 100 |
| Soda (30%) | qsp | pH5.5 |

These examples are not limiting. The basic gel can be prepared from substances conventionally used to make hydrogels suitable for the agro-alimentary field or for topical application (carragheens, xanthan gums and other polysaccharides, polyacrylates or polymethacrylates and their cross-linked derivatives such as carbomeres, sodium aluminum silicates, etc . . . ).

These compositions have a strong antimicrobial power which is based either on at least one alkane-1,2-diol alone, in sufficient concentration, or on the conjoint presence of at least one alkane-diol and of the glyceryl polymethacrylate gel. The pathogenic germs of the type Lysteria, Staphylococcus, Streptococcus, Pseudomonas, are inactivated very rapidly. The germs of the type Listerai inocua, which give rise to an undesirable taste when found in milk, are also inactivated. Thanks to the formation of a film of the gel on the skin of the teat, the antibacterial effect remains between two treatments. Moreover, the compositions have a very great hydrating power, they improve the condition of the skin, decrease wrinkles and chapping as well as irritations.

These alkane-1,2-diol base compositions, with or without gel of the glyceryl polymethacrylate type, can be added to any substance which is useful or conventionally preferred to be used in the field of the prevention of mastitis by dipping, spraying or massage of the teats: iodine or iodophores, chloramine T, hydrogen peroxide or other bactericidal substances, as well as any emollient and fatty substance (paraffin, synthetic or vegetal oils), healing substance (allantoin, bisabolol, karite butter, for example), or skin care product (plant extract). This list is not limiting.

The compositions according to the present invention, based on alkane-1,2-diol with or without gel of the glyceryl polymethacrylate type, thus find their use to obtain hydrogels adapted for the treatments and care of the skin, hair, nails and scalp, namely in particular anti-acne, anti-skin ailment, anti-impetigo, deodorant and anti-mycosal treatments.

With the addition of a fluidizing solvent, they can also be used to obtain hydrogels adapted for the treatment and the prevention of mastitis by topical application to the teats and udders of milk animals, to the decrease in risk of transmission of Listeria in milk, and to the improvement of the condition of the skin of the teat.

What is claimed is:

1. Cosmetic, dermopharmaceutical or veterinary compositions for topical application to the skin and having antimicrobial effect, comprising the combination of at least one alkane-diol of the general formula $$R-CHOH-CH_2-OH \quad (I)$$

in which R is a linear or branched 3 to 12 carbon alkyl chain and of a clathrate glyceryl poly(meth)acrylate gel comprising from 20 to 90% weight of glycerin, from 10 to 80% weight of water, and from 0.1 to 5% weight of polyacrylate and/or polymethacrylate, the gel having a viscosity comprised between 50,000 and 2,000,000 centipose.

2. Cosmetic, dermopharmaceutical or veterinary compositions according to claim 1, wherein the concentration of the alkane-diol varies between 0.1 and 5% by weight.

3. Cosmetic, dermopharmaceutical or veterinary compositions according to claim 1, wherein the alkane-diol is octane-1,2-diol.

4. Cosmetic, dermopharmaceutical or veterinary compositions according to claim 1, wherein the concentration of the glyceryl polymethacrylate gel varies between 1 and 99% by weight.

5. Cosmetic, dermopharmaceutical or veterinary compositions according to claim 1, wherein the glyceryl polymethacrylate gel is based on polymers derived from acrylic acid and/or methacrylic acid in the form of salts, esters or amides of said acrylic acid and/or said methacrylic acid.

6. Cosmetic, dermopharmaceutical or veterinary compositions according to claim 1, wherein they contain at least one fluidizing solvent of the general formula $$R_1-10-(R_2-O-R_2)_n-OR_3 \quad (II)$$

in which $R_1$ is a hydrogen atom or a straight chain or branched chain $C_{1-5}$ alkyl, $R_2$ is a linear or branched chain $C_{1-5}$ alkyl, $R_3$ is an atom of hydrogen or a straight or branched chain $C_{1-5}$ alkyl and n is a whole number between 1 and 200,000.

7. Compositions according to claim 6, wherein $R_1$ is a linear $C_{1-3}$ alkyl chain and n is a value between 1 and 3.

8. Compositions according to claim 6, wherein the proportion of fluidizing solvent is from 0.5 to 50%.

9. Compositions according to claim 1, wherein they are formulated into cosmetics, dermopharmaceuticals or for veterinary applications, by topical route and for antiseptic or antimicrobial use with a component from the group comprising aqueous solutions, oil/water emulsions and water/oil emulsions, milks, lotions, gels, pomades, capillary lotions, shampoos and rinses, soaps, sticks, sprays, masks, poultices, and dressings.

10. Compositions according to claim 1, combined with another ingredient conventionally used in the cosmetic, dermopharmaceutical or veterinary fields from the group comprising lipids of extraction or synthesis, gel-forming and thickener polymers, surface active agents and emulsifiers, hydrosoluble or liposoluble active principles, plant extracts, extracts, tissues, marine extracts, polyols, softeners, and other antimicrobial agents.

11. Compositions according to claim 1, further comprising a substance useful or ordinarily preferred to be used in the field of the prevention of mastitis in milk-bearing animals by immersion or massage of the teats from the group comprising iodine, iodophoes, chloramine T, hydrogen peroxide, other bactericidal substances, paraffin, synthetic or vegetal oils, other emollient and fatty substances, allantoin, bisabolol, karite butter, and plant extract.

12. Cosmetic, dermopharmaceutical or veterinary compositions according to claim 1, wherein the concentration of the alkane-diol varies between 0.1 and 1% by weight.

13. Cosmetic, dermopharmaceutical or veterinary compositions according to claim 1, wherein the concentration of the glyceryl polymethacrylate gel varies between 5 and 20% by weight.

14. Compositions according to claim 6, wherein the proportion of fluidizing solvent is from 1 to 10%.

15. A method of treatment or care comprising the step of topically applying on skin, hair, nails or scalp for anti-acne, anti-film forming, anti-impetigo, deodorant or anti-mycosal treatments, a composition comprising the combination of at least one alkane-diol of the general formula $$R\text{—}CHOH\text{—}CH_2\text{—}OH \qquad (I)$$

in which R is a linear or branched 3 to 12 carbon alkyl chain, and a clathrate glyceryl poly(meth)acrylate gel comprising from 20 to 90% weight of glycerin, from 10 to 80% weight of water, and from 0.1 to 5% weight of polyacrylate and/or polymethacrylate, the gel having a viscosity comprised between 50,000 and 2,000,000 centipose.

16. A method of treatment and prevention of mastitis for milk-giving animals, comprising the step of topically applying by dipping, spraying or massage of the teats and udders of said animals, for the decrease of the risk of transmission of Listeria in milk, and for the improvement of the condition of the skin of the teat, a composition comprising the combination of at least one alkane-diol of the general formula $$R\text{—}CHOH\text{—}CH_2\text{—}OH \qquad (I)$$

in which R is a linear or branched 3 to 12 carbon alkyl chain, and a clathrate glyceryl poly(meth)acrylate gel comprising from 20 to 90% weight of glycerin, from 10 to 80% weight of water, and from 0.1 to 5% weight of polyacrylate and/or polymethacrylate, the gel having a viscosity comprised between 50,000 and 2,000,000 centipose.

* * * * *